United States Patent [19]

Liston

[11] Patent Number: 4,528,159
[45] Date of Patent: Jul. 9, 1985

[54] AUTOMATED ANALYSIS INSTRUMENT SYSTEM

[75] Inventor: Max D. Liston, Irvine, Calif.

[73] Assignee: American Hospital Supply Corp., Evanston, Ill.

[21] Appl. No.: 400,191

[22] Filed: Jul. 20, 1982

Related U.S. Application Data

[63] Continuation-in-part of Ser. No. 284,842, Jul. 20, 1981, abandoned, which is a continuation-in-part of Ser. No. 284,841, Jul. 20, 1981, Pat. No. 4,477,190, which is a continuation-in-part of Ser. No. 284,840, Jul. 20, 1981, abandoned.

[51] Int. Cl.³ ............................................. G01N 35/04
[52] U.S. Cl. ..................................... 422/65; 356/244; 356/246; 422/63; 422/64; 422/67; 422/99; 422/100; 422/102; 435/805
[58] Field of Search .................... 422/63–67, 422/100, 99, 102; 435/805; 356/246, 244

[56] References Cited

U.S. PATENT DOCUMENTS

| | | | |
|---|---|---|---|
| 3,620,678 | 11/1977 | Guigan et al. | 422/66 |
| 3,770,382 | 11/1973 | Carter et al. | 422/65 |
| 3,883,305 | 5/1975 | Hoskins et al. | 422/65 |
| 4,101,284 | 7/1978 | Difiglio et al. | 422/100 |
| 4,234,538 | 11/1980 | Ginsberg et al. | 422/64 |
| 4,263,256 | 4/1981 | Morle | 422/66 |
| 4,338,279 | 7/1982 | Orimo et al. | 422/65 |
| 4,349,510 | 9/1982 | Kilehamainen et al. | 356/244 |

*Primary Examiner*—Michael S. Marcus
*Attorney, Agent, or Firm*—John H. Faro

[57] ABSTRACT

An automated instrument system for analyzing constituents of a patient sample while reacting a reagent specific for the selected constituent within the sample. The analyzer includes: a continuous flexible cuvette belt having a series of parallel discrete reaction compartments thereon, a carousel for dispensing solid tabletted reagents into the compartments, a means for effecting ultrasonic dissolution of the tabletted reagent in the reaction compartment, means for dispensing sample from a source thereof into a reaction compartment, including a sample source transport carousel assembly, and means for transporting the cuvette belt through a plurality of analysis stations located in a linear relationship along the path of travel of the cuvette belt.

40 Claims, 4 Drawing Figures

AUTOMATED ANALYSIS INSTRUMENT SYSTEM

CROSS REFERENCE TO RELATED APPLICATIONS

This application is a continuation in part of U.S. Application Ser. Nos. 284,842 (filed July 20, 1981) entitled "Cuvette System for Automated Chemical Analyzer" abandoned; 284,841 (filed July 20, 1981) entitled "Multichannel Spectrophotometer", now U.S. Pat. No. 4,477,190; and 284,840 (filed July 20, 1981), entitled "Loading and Transfer Assembly for Chemical Analyzer", abandoned.

INTRODUCTION

The present invention relates generally to an automated analysis instrument system and, more particularly, to an automated instrument for the analysis of a selected constituent of a specimen sample by reacting a reagent corresponding to the constituent with the sample. The present invention is particularly useful as an automated clinical chemistry analyzer for determining the presence and levels of one or more selected constituents in biological fluid samples.

BACKGROUND OF THE INVENTION

Numerous automated clinical analyzers are known and widely used in hospital clinical laboratories. The majority of such analyzers can be categorized into two distinct groups of either single-channel "batch" type analyzers or multi-channel "profile" type analyzers. Batch type analyzers are adapted to test for a single constituent in each of multiple samples loaded into the instrument. An example of such an instrument is illustrated in U.S. Pat. No. 3,748,044 issued to the same inventor herein. By contrast, profile type analyzers simultaneously test for a fixed number of predetermined different constituents in each of multiple samples loaded into the instrument. Such testing for multiple constituents is generally accomplished by dividing the sample and passing these portions through separate and discrete analysis stations or channels (hence the designation "multi-channel"). Each of these analysis stations is generally dedicated to testing the sample for a particular constituent.

Both the batch and profile type analyzers generally utilize a liquid reagent with the particular constituent being tested in the sample and a photo-optical system to read the optical absorbance of the sample which corresponds to the level of the constituent in the sample.

Although each of these types of automated analyzers have received wide acceptance in the clinical laboratory, certain drawbacks are associated with their use. For example, although the batch type analyzer is reliable due to its simplicity, cost effective for large number of samples and has a relatively high test throughout rate, it is limited in the sense that it can only be effectively utilized to perform a single constituent analysis at a time on a relatively large number of samples. In addition, such analyzers are not capable of performing emergency "stat" tests due to their relatively long and complex set up time and their inherent inability to economically analyze a single test sample.

Profile type analyzers are similarly limited in their ability to perform emergency "stat+ tests. A further significant disadvantage found with profile type analyzers is that although they can simultaneously perform tests for multiple constituents on the same sample, generally all of these tests must be performed for every sample whether desired or not. This results in a waste of both sample material and the reagents used in the unnecessary tests. Furthermore, due to the fact that multiple discrete and dedicated channels are utilized in such an instrument, there is significant duplication of numerous components which adds to the complexity and expense of the overall instrument.

BRIEF DESCRIPTION OF THE INVENTION

The automated analysis instrument system of the present invention overcomes the above-described drawbacks found with known analyzers by providing a simple and accurate instrument that can perform one or multiple selected tests on a single specimen and which does not require any appreciable test set up time so that it is available at any hour of the day for either stat testing of emergency samples or for routine chemistries. The unique design of the present invention incorporates extreme flexibility, availability and simplicity of operation with a high test throughout rate, low per test cost and positive sample identification.

The present system utilizes a disposable cuvette belt which is formed form a thin plastic film. A series of parallel discrete reaction chambers are formed in this flexible belt which transports the reaction mixtures through the instrument. A preferred embodiment of this cuvette belt is described in commonly owned U.S. patent application Ser. No. 284,842, filed July 20, 1981, entitled "Cuvette System for Automated Chemical Analyzers," the disclosure of which is incorporated by reference herein. Such a cuvette belt provides a simple and highly flexible means for transporting the reaction mixtures through the instrument in such a manner that multiple photometer readings may be made on each reaction mixture at selected time intervals without the necessity of passing the mixture back through an analysis station a second time. The disposable cuvette belt also avoids the requirement for washing the reaction chambers which requires additional hardware. Furthermore, it provides completely discrete handling of the reaction mixtures thereby avoiding the possibility of cross-contamination which is associated with flow-through cuvettes and the possibility of incomplete washing of reusable discrete reaction chambers which may lead to inaccurate tests results.

In conjunction with the cuvette belt, the analyzer of the present invention utilizes a unique photo-optical system employing fiber optical bundles or similar light guides to transmit various wavelengths of light to each analysis station from a single light source. It is to be noted that the term "light" as used herein should be considered in its broadest sense to include both visible wavelengths and non-visible spectral analysis wavelengths. A preferred embodiment of this photo-optical system is described in commonly owned U.S. patent application Ser. No. 284,841, filed July 20, 1981, entitled "Multichannel Spectrophotometer," the disclosure of which is incorporated by reference herein.

In addition to sharing a single light source, the photo-optical system also shares common wavelength selective filters at both the output and input sides of the system. In this manner, a further reduction in the cost and complexity of the system is achieved and the reliability of the instrument is not degraded to the same extent when utilizing a large number of photometers as compared to using a separate light source and filter combination for each photometer. Furthermore, in large part due to the fact that a single wavelength determining light source/filter element for each wavelength is used regardless of the analysis station where the reading is physically being made, it is possible to obtain extremely precise "tracking" or correspondence between the spectral responses of the photometric readings from each of the stations. In this connection, it has been found that a one percent coefficient of variation can be achieved between the analysis station photometer responses when read in milliabsorbance units carried to the fifth decimal place. Such precision is necessary, for example, for comparing kinetic deltas (rates of change in spectral absorption) for high density "down" rate reactions where very small changes must be measured in the presence of strong absorbances.

In the preferred embodiment, eight analysis stations are located from 0 to 10 minutes of reaction incubation time along the cuvette track and tests my be read at any or all of these stations. Each fiber optic bundle can transmit up to 150 pulses at each of seven separate wavelengths of light to all eight read stations during each five-second period in which a particular cuvette is positioned in a progressive stepped manner at each of the read stations. However, due to the position-to-position transit time of the advancing cuvettes, each cuvette is stationary for only about four seconds at each read station. Hence, only approximately 100 pulses are usable for analysis purposes. A microprocessor selects two appropriate wavelengths for conducting bichromatic analysis of the selected sample constituent at each of the eight read stations. Absorbance measurements are then made at the appropriate endpoint or optimal zero order kinetic time periods. During calculations, the microprocessor may determine that the sample should be further diluted or flag the test result due to inherent sample absorbance (e.g., interfering icterus, lipemia or hemolysis) that could result in an inaccurate test result with certain constituent analyses.

One of the principle features and advantages of the present invention is that the multiple analysis stations permit their positioning at read times that are closely related to theoretical optimal kinetic and endpoint reaction read times. Futhermore, each of the analysis stations is capabile of utilizing any combination of the seven wavelengths to analyze the sample, thereby avoiding the inherent disadvantages found with prior art dedicated analysis tracks. For example, the multiple analysis stations allow read-time flexibility for up to ten minutes at any selected wavelengths with kinetic reactions which permits the microprocessor to monitor these reactions and select appropriate zero order delta readings from a series of readings obtained from the different analysis stations. This capability and flexibility is also useful for sera blanking determinations which may be utilized to correct substrate depletion flag points in kinetic reactions so as to provide a larger useful range for the chemistry methodology used and to substract out chromogens naturally occuring in the sample in order to set zero levels for endpoints reactions.

It has been found with the five second cuvette advance rate mentioned above that adequate time is provided for sample, reagent and diluent dispensing, mixing of the reaction mixture and photometry operations. This cuvette belt advance rate results in the capability of providing 720 tests per hour. Since the same optical analysis may be performed on a particular sample up to eight times as the sample cuvette moves through the instrument, it is not necessary to hold work up at any one station until a particular test is completed. Hence, although the testing is performed methodically, it is accomplished at optimum speed to provide high throughout without compromising test accuracy and reliability. Furthermore, since the microprocessor will print out a test result as soon as it is completed regardless of the status of other tests being performed by the instrument which may required more time, stat results are obtained as soon as possible.

Another important feature of the present invention is that it is adapted to efficiently utilize dry reagents, preferably in tablet form. Such tablets are dropped into the cuvette by the operation of a tablet dispenser mounted on a rotating carousel which holds a large number of tablets in a ready state. A preferred embodiment of such a tablet dispenser is described in commonly owned U.S. patent application Ser. No. 285,022, filed July 20, 1981, entitled "Tablet Dispensing Device, " the disclosure of which is incorporated by reference herein.

Such tabletted reagents are always ready for use so that there is no warm-up or set-up time necessary for stat testing. Since tablet dispensers for numerous chemistries can be held in a simple, mechanical carousel which, under microprocessor control, will rotate the appropriate dispenser into position over the cuvette and drop a tablet, it is not necessary for the operator to select, measure or mix reagents and the valving, tubing and other plumbing needs of the system are greatly reduced. Furthermore, since the reagent tablet is only reconstituted when needed for a particular analysis and then in only a precise amount for that particular test, there is no waste of reagent. Hence, unlike profile analyzers, only the particular tests desired and seleced are conducted by the instrument, thereby eliminating reagent and sample waste.

Furthermore, dry reagents inherently have a significantly longer stability life over reconstituted liquid reagents and, hence, do not require removal from the instrument for storage and refrigeration when not in use. An added benefit is that the analyzer is not locked into a fixed test format with inflexible analyzer hardware. Tablet dispensers for new chemistries can simply be inserted into reagent carousel and, after the microprocessor software is electronically updated with the new test data, they are ready to be conducted by the instrument.

Another significant advantage of the automated analysis system of the present invention is that it permits the effective use of a microprocessor-controlled loading and transfer assembly for presenting to the analyzer containers having the samples to be tested. A preferred embodiment of such a loading and transfer assembly is described in commonly owned U.S. patent application Ser. No. 284,840, filed July 20, 1981, entitled "Automated Analysis Instrument System," the disclosure of which is incorporated by reference herein.

Such a loading and transfer assembly can be adapted to identify the sample as it is presented to the analyzer and feed this information to the microprocessor controlling the dispensing of the reagents so that the desired tests are performed on the sample. In addition, since such an assembly permits utilization of the same container in which the sample was collected (i.e., in the case of blood samples, the "Vacutainer" tube which is commonly used to draw the sera specimen), the identification of the sample is positive without the possibility of intervening human error in the transfer or loading of the sample into the analyzer.

Other features and advantages of the present invention will become apparent to those skilled in the art when viewing the attached drawings taken in conjunction with the following description of the preferred embodiment of the invention.

DESCRIPTION OF THE PREFERRED EMBODIMENT

Figure 1:
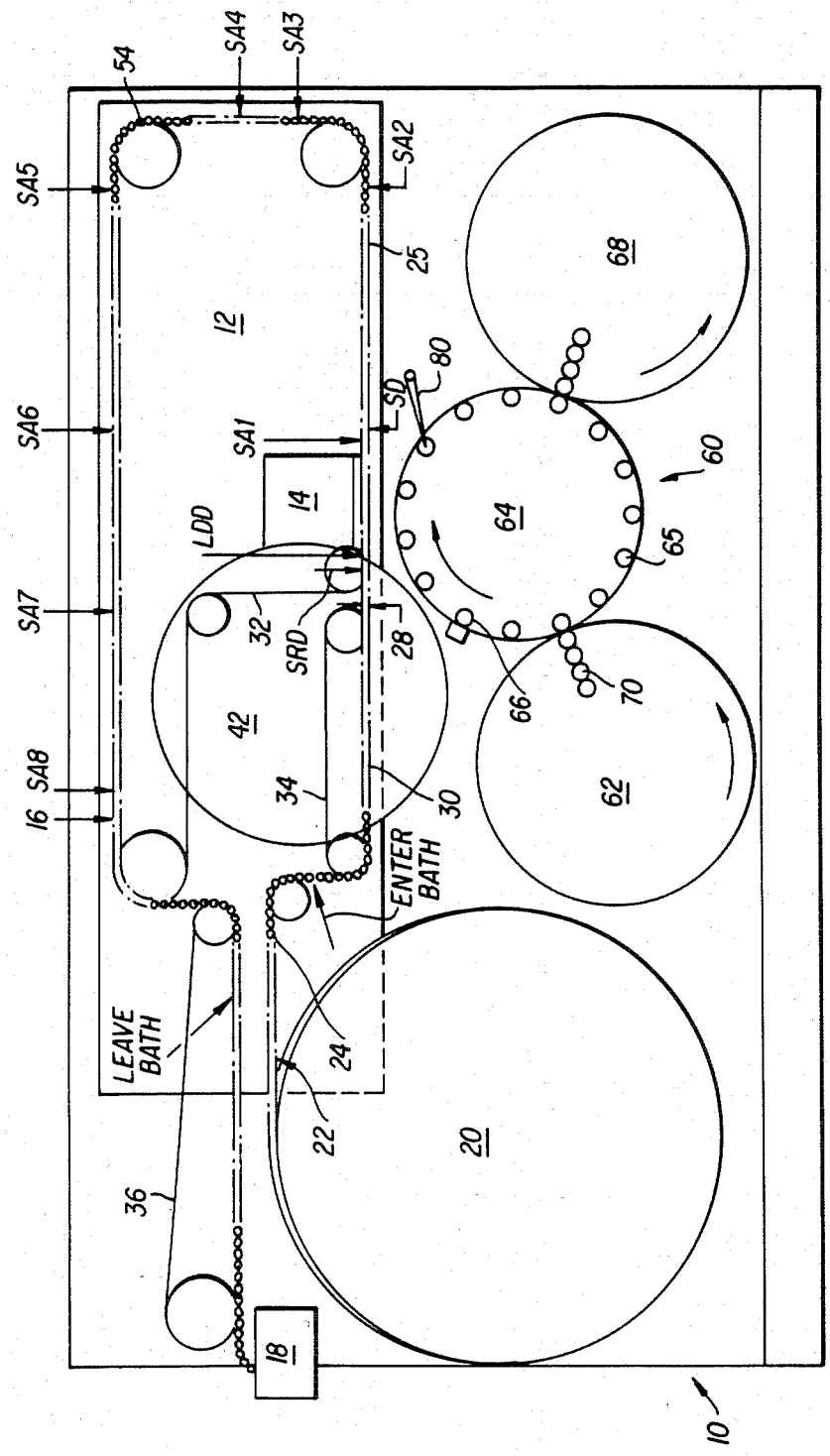
FIG. 1 is to top schematic view of an automated analysis instrument system constructed in accordance with an embodiment of the present invention.
Figure 2:
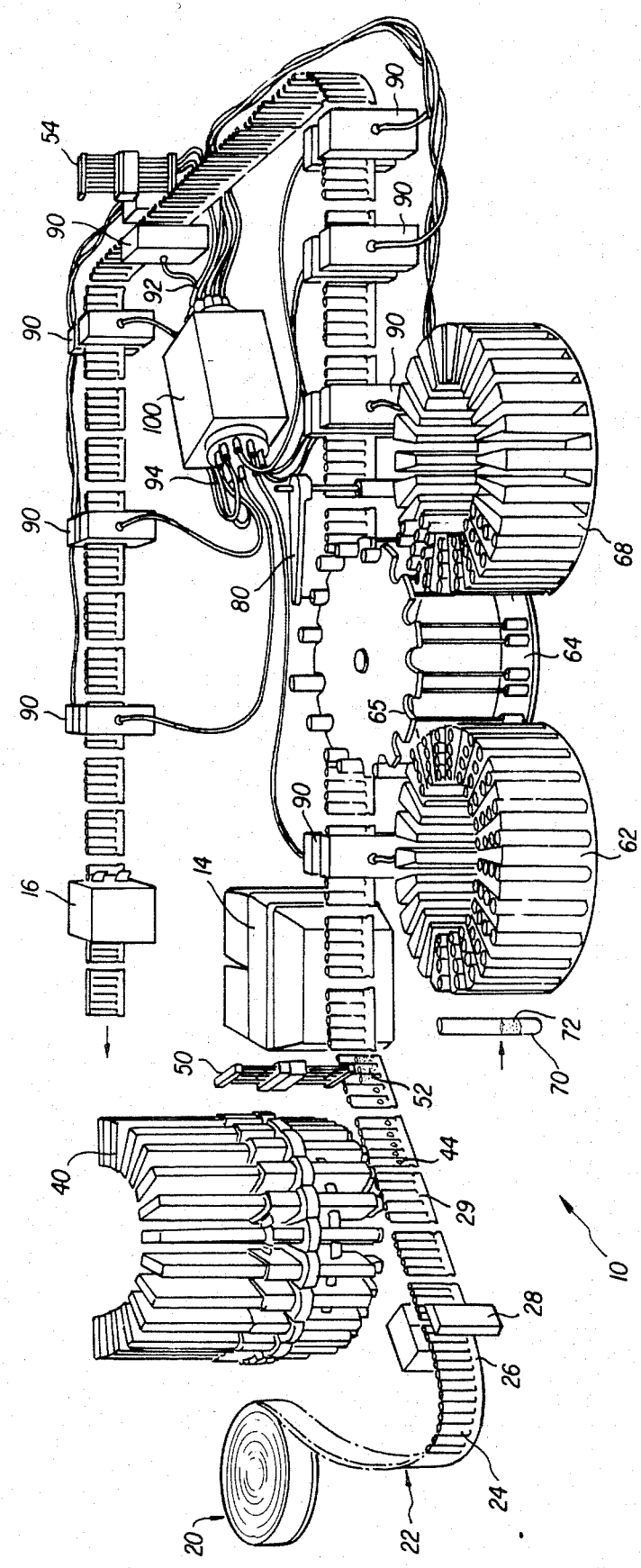
FIG. 2 is a partial perspective view of the analysis system of FIG. 1 showing many of the important operational features thereof.

Referring to FIGS. 1 and 2, an automated analysis instrument system 10 is shown in which is constructed in accordance with an embodiment of the present invention. In this embodiment, the system is configured as clinical analyzer for the testing of constituents in biological fluids, such as blood samples.

The systems generally comprises the following elements:

(A) A disposable reaction cuvette supply 20 consisting of a continuous cuvette belt 22 having a series of parallel discrete reaction compartments 24 formed in a spaced relationship therein.

(B) A single continuous cuvette track 30 having a main transport belt 32 disposed therein which engages indexing holes 26 formed in cuvette belt 22 and advances the reaction compartment 24 at a predetermined rate of advance through the instrument.

(C) A series of tabletted reagent dispensers 40 located in a rotatable dispenser carousel 42 which is adapted to bring the correct reagent dispenser 40 to solid reagent dispensing point "SRD" where a single reagent tablet 44 is dropped into a reaction compartment.

(D) A diluent and/or liquid reagent dispenser 50 is located adjacent to carousel 42 for adding sufficient diluent 52 for reagent tablet 44 dissolution and/or for dispensing a liquid reagent into the reaction compartment 24 at point "LDD".

(E) A sample loading and transfer carousel assembly 60 is located downstream of the reagent and diluent dispensers. This carousel assembly comprises a loading carousel 62 into which patient samples 70 are randomly loaded; a transfer carousel 64 which accepts the patient samples 70 from loading carousel 62, identifies the patient sample by means of a bar code reader 66 which reads a bar code label 72 placed on the patient sample container and continuously feeds the patient samples into the system; and finally, an unloading carousel 68 receives the patient samples 70 after testing and stores them in an organized manner in the event that they must later be located and retrieved.

(F) Sampler 80 for dispensing sample into the reaction compartments 24 at point "SD" is located adjacent to transfer carousel 64. This sampler is designed to aspirate 2 to 20 $\mu$l of patient sample 70 from its container in the transfer carousel and dispense it into a reaction compartment 24 every five seconds.

Figure 3:
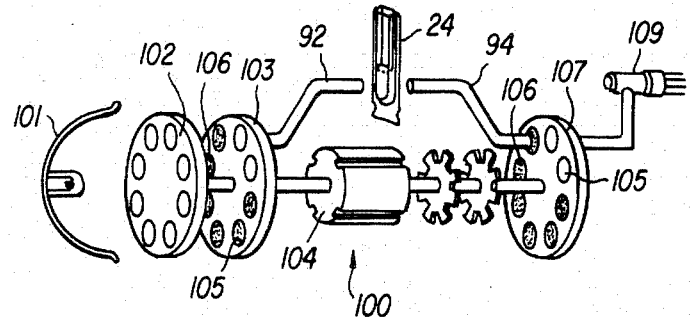
FIG. 3 is a partial schematic representation of a preferred photo-optical system utilized with the analysis system of FIGS. 1 and 2.

(G) Eight photometric analysis stations 90 are located at points "SA1" through "SA8" along the cuvette track 30. These analysis stations are connected by individual optical guides 92 and 94 to photo-optical system 100. This system is illustrated in FIG. 3 and is described in detail below.

Turning now to the detailed operation of the instrument system, a phlebotomist draws a patient blood sample 70 which is positively identified by a bar code label 72 placed on the container in which the sample is drawn. After centrifuging the sample to separate the sera, the sample along with as many others as desired is placed in loading carousel 62 which is then placed into the instrument loading and transfer carousel assembly 60. For emergency stat testing, the patient sample 70 may be loaded directly into one of the empty sample receiving slots 65 of transfer carousel 64, or may be exchanged with a sample container already loaded in transfer carousel 64 prior to bar code reader 66.

The loading carousel is then automatically indexed to a position where the patient sample 70 is transferred into an empty sample receiving slot 65 of transfer carousel 64. The transfer carousel 64 then indexes around to bar code reader 66 which identifies the patient sample. This sample identity is fed to an instrument control microprocessor (not shown) which correlates this information with the test requisition for this sample that has already been entered into the instrument computer system by the laboratory technician.

The control microprocessor then begins the advance of the cuvette supply reel 20 and belt 22 into cuvette track 30 in response to this sample identification. This cuvette supply advance is accomplished by loading belt 34 which threads the cuvette belt into main transport belt 32. If bar code reader 66 detects that there are no further samples to be tested, the control microprocessor will activate cuvette belt cutter 28 which divides cuvette belt 22 into sections 29 having a number of reaction compartments corresponding to the number of analysis reactions to be performed at a given time. This procedure minimizes waste for single tests or stat situations. In addition, the cuvette belt cutter 28 may also be periodically operated during continuous operation of the instrument in order to prevent the length of the cuvette belt (which must be disposed of) from becoming unmanageable.

As it is fed into the instrument, the cuvette belt 22 enters a water path 12 which will maintain the reagent and sample reaction mixture at a predetermined incubation temperature. This reaction temperature is generally either 30 degrees C. or 37 degrees C.

For the sake of simplicity, it should also be noted that in FIG. 1, each circular cuvette position point 25 along cuvette track 30 represents a 5 second period. In other words, every 5 seconds the control microprocessor will step a particular cuvette reaction compartment 24 to the next circular position along the cuvette track 30.

During the time that the transfer carousel 64 is indexing the sample 70 between the bar code reader 66 and its position where sampler 80 aspirates a portion thereof, an appropriate reagent is added at either point "SRD"

and "LDD" to the reaction compartment that is timed by the control microprocessor to receive the sample. The microprocessor causes the proper reagent to be dispensed from one of the thirty-two different tabletted reagent dispensers 40 that can be accommodated by dispenser carousel 42, or the multiple liquid reagents that can be accommodated by diluent/liquid reagent dispenser 50, in response to the patient sample identification by bar code reader 66.

If a tabletted reagent is dispensed, sufficient diluent for tablet dissolution is added thereto at point "LDD" and an ulatrasonic horn 14 is utilized to provide 45 seconds of high energy ultra-sound to completely break up and dissolve the reagent tablet. In the preferred embodiment, this reagent mixture has a volume of 200 $\mu$l.

After this reconstitution of the reagent in the predetermined amount of diluent, the reaction compartment is passed to a reagent quality control analysis station at point "SA1". Here each reagent mixture is photometrically analyzed to verify proper reagent dispensing and dissolution. Furthermore, the microprocessor can also utilize this reading to adjust for any minor variation in reagent amount and resulting concentration that may exist from tablet to tablet.

Next, the reaction compartment 24 is transported to point "SD" where sampler 80 will dispense the appropriate patient sample into the reaction compartment 24. As noted above, the main transport belt 32 of cuvette track 30 is carefully synchronized with the reagent dispensers and the sampler to insure that the proper reaction mixture is obtained as ordered by the control microprocessor. Since sampler 80 is the only non-discrete element of the analysis system, its probe is flushed with additional diluent to prevent contamination and carry-over between samples. In the preferred embodiment, the final reaction volume is 300 $\mu$l.

The next analysis station is the sample blanking station located at point "SA2". It has been found desirable to dispense an amount of each patient sample into a reaction compartment without a reagent being added to obtain a sample blank. This sample blank value may be obtained at this analysis station or any of the following six analysis stations as required.

A second reagent dispenser 54 may be located further down the cuvette track 30 for multiple or triggered reaction capability. For example, such a reagent dispenser would be useful in conducting CKMB constituent analyses.

At the end of the cuvette track 30, a cuvette sealer 16 is located to seal the tops of the cuvette reaction compartments after testing for convientent and sanitary disposal of the samples. After passing through the cuvette sealer 16, the cuvette belt 22 is stripped off of the main transport belt 32 by an unloading belt 36 which removes the tested cuvettes from the water bath 12 and automatically discards them into disposal bin 18.

As referred to above, all eight analysis stations are connected via light guides 92, 94 to photo-optical system 100. The principal elements of this system are shown in FIG. 3. The photo-optical system comprises a single light source 101 for generating selected wavelengths of light. The output of light source 101 is focused by fixed focusing lens 102 onto the multiple wavelength selective filters disposed about the circumference of rotary source filter wheel 103. The rotation of source filter wheel 103 is regulated by the instrument control microprocessor through double shafted motor 104. The output from source filter wheel 103 is sequentially transmitted through separate light guides 92 to each of the analysis stations.

At the analysis stations, the filtered light energy is passed through the reaction compartment 24 containing the mixture to be analyzed, and the output of the analysis is then passed back to the photo-optical system 100 via separate light guides 94. At this point, a second filter wheel 107, which preferably is identical to and synchronized with source filter wheel 103, intercepts the outputs of light guides 94 before this output is directed to a separate photodetector tube 109 for each analysis station. A reflector 108 may be utilized to focus the output of filter wheel 107 on photodetector tubes 109. In the representation of FIG. 3, only one set of light guides 92, 94 and one photodetector tube 109 is shown for simplicity, although it is to be understood that eight of these elements (one for each analysis station) are required.

The outputs of photodetector tubes 109 are monitored by the control microprocessor and appropriate wavelength output values for each analysis reaction at each analysis station is stored by the microprocessor. When the reaction is completed, the microprocessor will utilize this stored information to calculate the concentration of the selected sample constituent and provide this result to the instrument operator.

As can be seen from FIG. 3, each filter wheel has seven different wavelength selective filters 105 disposed about its circumference. In addition, an opaque blank 106 is located thereon in order to establish the residual "dark current" level of the electronics. Hence, great flexibility is provided by permitting any one or combination of the seven wavelengths to be read at any analysis station for any sample during the four second analysis period. In that filter wheels 103, 107 are rotated at thirty revolutions per second in the preferred embodiment, thirty readings at a particular wavelength may be made each second which can them be averaged to provide a highly accurate final value by the microprocessor.

Figure 4:
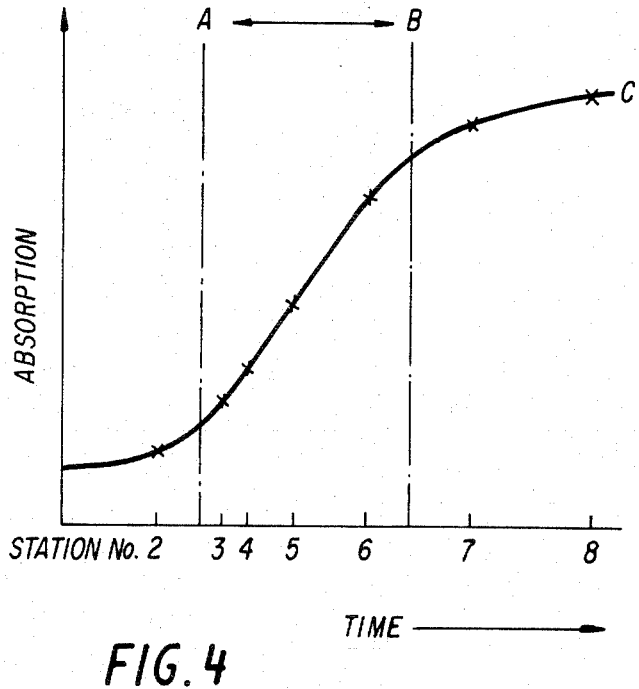
FIG. 4 is a diagram of a typical kinetic analysis reaction showing a preferred utilization of the present invention.

FIG. 4 illustrates a typical kinetic zero delta reaction which will help to illustrate the analytical abilities of the present invention. The vertical axis of the graph is in increasing absorbance units while the horizontal axis is in increasing time units, from 0 to 10 minutes. The reading times of analysis station point "SA2" through "SA8" as the sample is transported through the instrument are shown along this horizontal axis. The actual continuous absorption curve for the kinetic reaction (such as for a CPK test) is labeled "C".

In such kinetic analysis, the linear portion of this absorbance curve between points A-B are usable to calculate the level of the constituent being analyzed. However, these points are not fixed and will vary from sample to sample and constituent to constituent. Hence, in order to determine the linear portion of the absorption curve, the microprocessor will compare the deltas (rate of change in absorption or the slope of curve C) of adjacent analysis stations for the selected wavelengths used in the analysis (usually two for bichromatic testing). When two or more of these deltas between three or more stations becomes approximately the same (or the rate of change there between become approximately zero, hence, the term "delta zero"), curve C will be linear at these points and the resulting absorption values may be used to accurately calculate the constituent level in question.

From this example, the great flexibility and analytical power of the present invention in providing multiple analysis stations that are staggered in read time along with the capability of utilizing any combination of seven different analysis wavelengths at each station can be appreciated.

Although particular configurations and features of the present invention have been discussed in connection with the above-described preferred embodiment thereof, it should be that those skilled in the art may make various changes, modifications and substitutions thereto without departing from the spirit of the invention as defined by the following claims. For example, it should be evident from the above discussion that an instrument constructed in accordance with the present invention could be adapted for analyzing a wide range of different specimen types where it is required that such specimens be reacted for differing, predetermined periods of time and that analytical readings be taken during or at the end of these time periods.

What is claimed is:

1. An automated instrument system for analyzing the constituents of a patient sample while reacting a reagent specific for the selected constituent within said sample, the system comprising:
    (a) a continuous flexible cuvette belt comprising a series of parallel, discrete reaction compartments formed in spaced relationship therein, each of said discrete reaction compartments being substantially optically transparent, having an open top end and a closed bottom end and adapted for engagement by a cuvette track;
    (b) carousel means for dispensing solid tabletted reagents into said discrete reaction compartments of such cuvette belt, said tabletted reagents being stored in a series of tablet dispensers within the carousel;
    (c) means for effecting ultrasonic dissolution of said tabletted reagents, said means being positioned along a cuvette track between the carousel means for dispensing solid tabletted reagents and the means for dispensing sample;
    (d) means for dispensing sample from a patient sample container into said discrete reaction compartments of said cuvette;
    (e) means for transport of the patient sample container including a carousel assembly located downstream from said reagent dispenser, said carousel assembly comprising:
        (i) a loading carousel into which patient sample containers can be randomly loaded,
        (ii) a transfer carousel which accepts patient sample containers from the loading carousel and positions them in cooperative relation with the sample dispensing means, said transfer carousel including means for identifying said patient sample container from coded information contained on said sample container, and
        (iii) an unloading carousel which receives patient sample containers from the transfer carousel subsequent to transfer of a portion of the sample to a discrete reaction compartment of the cuvette belt;
    (f) a plurality of analysis stations arranged in linear relationship to one another along a track for advancement of the cuvette belt; and
    (g) means for transporting, at a pre-determined rate, said cuvette belt along a continuous cuvette tract past a plurality of analysis stations.

2. The analysis system of claim 1 wherein said cuvette transport means comprises a track having a means disposed therein for engaging and advancing said cuvette compartments.

3. The analysis system of claim 2 wherein at least a portion of said cuvette transport track is disposed in means defining a water bath for maintaining said reagent and sample reaction mixture at a predetermine incubation temperature.

4. The analysis system of claim 2 wherein said cuvette compartment engaging and advancing means advances said reaction compartments in a stepped manner whereby said reaction compartments are held stationary at said analysis stations for a fixed period of time before being advanced to their next stepped position.

5. The analysis system of claim 4 wherein the number of stepped positions of said reaction compartments between said analysis stations corresponds to desired periods during the reagent reaction times for analyzing said selected constituents.

6. The analysis system of claim 1 further comprising a means for dividing said cuvette belt into sections having a number of reaction compartments corresponding to the number of analysis reactions to be performed at a given time.

7. The analysis system of claim 6 wherein said dividing means comprises cuvette belt cutter.

8. The analysis system of claim 6 further comprising a means for feeding said cuvette belt sections into said cuvette transport track.

9. The analysis system of claim 8 wherein said cuvette feeding means comprises a portion of said cuvette transport track having a separate cuvette belt engaging and advancing means disposed therein.

10. The analysis system of claims 6 wherein said cuvette belt dividing means is operated in response to said sample identifying means.

11. The analysis system of claim 10 further comprising a means for feeding said cuvette belt sections into said transporting means in response to said sample identifying means.

12. The analysis of claim 1 wherein said analysis stations comprises a photo-optical system to analyze said reagent and sample reaction.

13. The analysis system of claim 12 wherein said photo-optical system is bichromatic.

14. The analysis system of claim 12 wherein said photo-optical system comprises a single light source for generating selected wavelengths of light and separate light guides for transmitting said light wavelengths to each of said analysis stations.

15. The analysis system of claim 14 wherein said light guides are fiber optical bundles.

16. The analysis system of claim 14 wherein said light guides are fluid filled light pipes.

17. The analysis system of claim 14 further comprising common wavelength selective filters for sequentially transmitting said selected wavelengths of light through said light guides to each of said analysis stations.

18. The analysis system of claim 17 wherein said common wavelength selective filters are segments of a rotary source filter wheel, the selected wavelength of light output of each filter segment being sequentially directed to said separate light guides for transmission to said analysis stations.

19. The analysis system of claims 17 wherein said different wavelengths of light transmitted to each of said analysis stations are selected to response to said sample identifying means.

20. The analysis system of claim 14 further comprising a second set of separate light guides for directing the outputs of each said analysis stations to photodetector means.

21. The analysis system of claim 20 further comprising a second set of common wavelength selective filters sequentially intercepting the outputs of said separate light guides before being directed to said photodetector means.

22. The analysis system of claim 21 wherein said second set of common wavelength selective filters are segments of a rotary detector filter wheel.

23. The analysis system of claims 22 wherein said source and detector filter wheels are rotated in aligned synchronism with each other.

24. The analysis system of claim 23 wherein said source and detector filter wheels have identical filter segments.

25. The analysis system of claim 1 wherein said reagent is in a solid form.

26. The analysis system of claim 25 wherein said solid reagent is formed into a single tablet.

27. The analysis system of claim 26 wherein said reagent tablet is stored in a dispenser containing a number of identical reagent tablets, said dispenser being adapted to drop said tablets one at a time into said cuvette reaction compartments.

28. The analysis system of claim 27 further comprising means positioned along the cuvette track subsequent to the tablet dispensing means and in advance of the ultrasonic dissolution means for dispensing diluent into said cuvette compartment containing tabletted reagent.

29. The analysis system of claim 28 further comprising a means for mixing said reagent tablet and diluent in said compartment.

30. The analysis system of claim 29 wherein said mixing means comprises an ultrasonic horn.

31. The analysis system of claims 30 wherein said ultrasonic horn is disposed within said water bath.

32. The analysis system of claims 28 wherein said diluent is dispensed into said cuvette compartment in response to said sample identifying means.

33. The analysis system of claim 1 further comprising a means for identifying each of said samples.

34. The analysis system of claim 33 wherein multiple different reagents are contained in said instrument and said reagent dispensing means further comprises a means for selecting one or more of said reagents for dispensing into said cuvette compartment in response to said sample identifying means.

35. The analysis system of claims 33 wherein said sample is dispensed into said cuvette compartment in response to said sample indentifying means.

36. The analysis system of claims 33 wherein the output of said photodetector means is read in response to said sample identifying means.

37. The analysis system of claim 36 further comprising a means to store the output readings of said photodetector means.

38. The analysis system of claim 37 further comprising a means to calculate the concentration of said selected sample consituent from the photometer output readings in said storage means.

39. The analysis system of claim 38 wherein said calculating means selects certain of said photometer output readings in said storage means corresponding to three or more adjacent analysis stations to establish absorption deltas for zero order kinetic reactions.

40. The analysis system of claim 39 wherein said calculating and storage means comprise a microprocessor.

* * * * *